United States Patent
Smith

(10) Patent No.: US 8,911,412 B2
(45) Date of Patent: Dec. 16, 2014

(54) INTERLOCK MECHANISM FOR A DRUG DELIVERY DEVICE AND DRUG DELIVERY DEVICE

(75) Inventor: Christopher James Smith, Holmes Chapel (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 260 days.

(21) Appl. No.: 13/139,918

(22) PCT Filed: Dec. 17, 2009

(86) PCT No.: PCT/EP2009/067388
§ 371 (c)(1),
(2), (4) Date: Nov. 3, 2011

(87) PCT Pub. No.: WO2010/070040
PCT Pub. Date: Jun. 24, 2010

(65) Prior Publication Data
US 2012/0041364 A1    Feb. 16, 2012

(30) Foreign Application Priority Data
Dec. 19, 2008    (EP) .................................... 08022179

(51) Int. Cl.
*A61M 5/315* (2006.01)
*A61M 5/20* (2006.01)

(52) U.S. Cl.
CPC ............. *A61M 5/31591* (2013.01); *A61M 5/20* (2013.01)
USPC .......................................... 604/223; 604/228

(58) Field of Classification Search
None
See application file for complete search history.

(56) References Cited

U.S. PATENT DOCUMENTS

| | | | |
|---|---|---|---|
| 2,671,347 A * | 3/1954 | Scherer ................................. | 74/2 |
| 5,865,804 A | 2/1999 | Bachynsky | |
| 6,241,709 B1 | 6/2001 | Bechtold et al. | |
| 6,599,272 B1 * | 7/2003 | Hjertman et al. ............. | 604/209 |
| 6,972,007 B2 | 12/2005 | Geiser et al. | |
| 8,167,849 B2 * | 5/2012 | Boyd et al. ..................... | 604/208 |

FOREIGN PATENT DOCUMENTS

| | | |
|---|---|---|
| WO | 02/47746 | 6/2002 |
| WO | 2006/045529 | 5/2006 |
| WO | 2006/130098 | 12/2006 |
| WO | 2007/063342 | 6/2007 |

OTHER PUBLICATIONS

International Preliminary Report on Patentability for International App. No. PCT/EP2009/067388, dated Jun. 21, 2011.
International Search Report for International App. No. PCT/EP2009/067388, mailed Apr. 8, 2010.

* cited by examiner

*Primary Examiner* — Nicholas Lucchesi
*Assistant Examiner* — Weng Lee
(74) *Attorney, Agent, or Firm* — McDonnell Boehnen Hulbert & Berghoff LLP

(57) ABSTRACT

The invention refers to an interlock mechanism for restricting a rotational movement of a rotatable component (1) of a drug delivery device (10) and to a method for controlling the rotational movement of the rotatable component (1). The method comprises the steps of:
translatively moving a trigger arm (6) engaged with a protrusion (7) of a latch arm (5) from an initial position for pivoting the latch arm (5) out of one of at least one catches (3) provided in a cam profile of the rotatable component (1) thus allowing the rotatable component (1), biased by an energy source, to rotate;
pivoting the trigger arm (5) by one of at least one cams (4) provided in the cam profile during the rotation (R) of the rotatable component (1) whereby the trigger arm (6) is disengaged from the protrusion (7) thus allowing the latch arm (5) to re-engage with one of the catches (3) to stop the rotational movement (R) and whereby an interlock means (8) catches and holds the trigger arm (6) in its translatively moved and pivoted position until the interlock means (8) is released by a reset means;

translatively moving the trigger arm (6) back into the initial position once the interlock means (8) is released thereby allowing it to pivot back and re-engage with the protrusion (7).

13 Claims, 2 Drawing Sheets

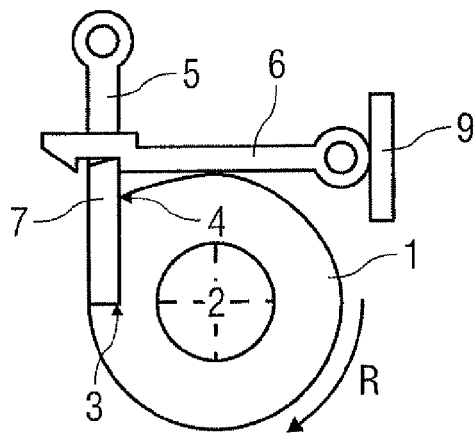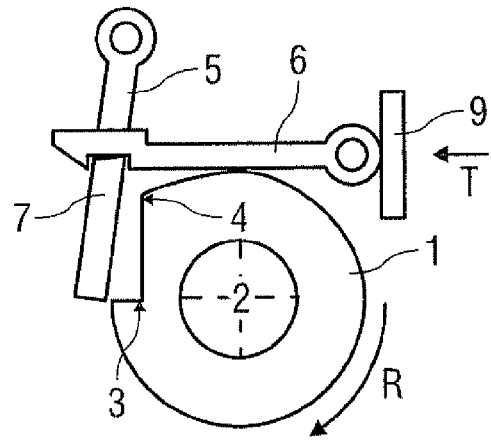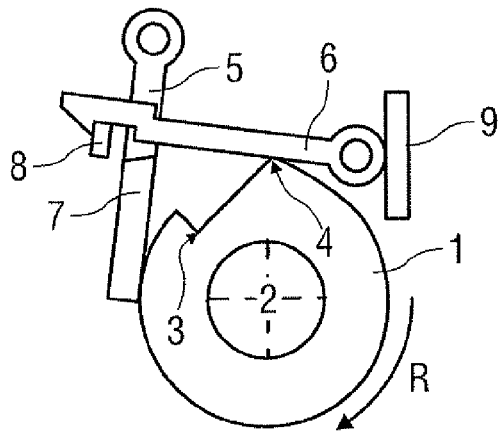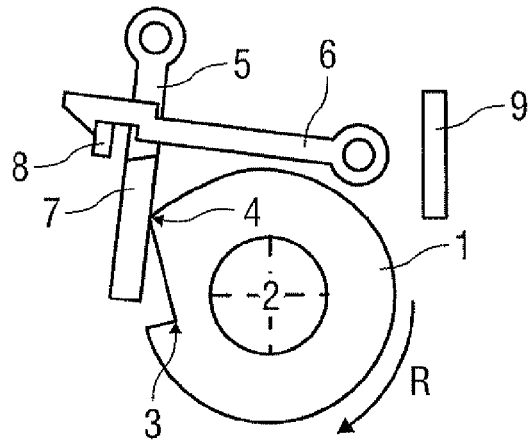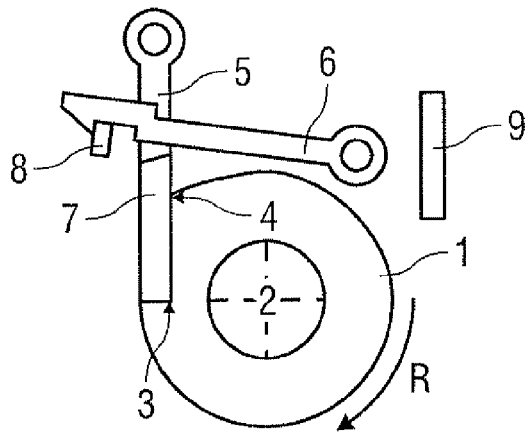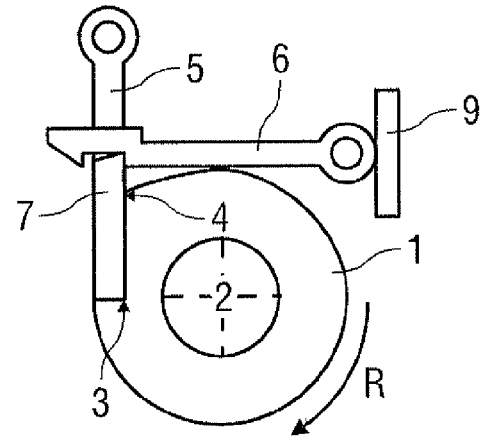

US 8,911,412 B2

INTERLOCK MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2009/067388 filed Dec. 17, 2009, which claims priority to EP Patent Application No. 08022179.9 filed on Dec. 19, 2008. The entire disclosure contents of these applications are herewith incorporated by reference into the present application.

FIELD OF THE INVENTION

The invention refers to an interlock mechanism for restricting a rotational movement of a rotatable component of a drug delivery device. The invention also refers to a drug delivery device provided with such an interlock means. Furthermore, the invention refers to a method for controlling the rotational movement of the rotatable component of the drug delivery device by the interlock mechanism.

BACKGROUND

Autoinjector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Autoinjectors require some form of energy input in order to operate. Typically this is achieved by the user performing a "priming" or "cocking" action prior to the injection. This may make the device more complicated to use, as it increases the number of user steps. Also, the actions required, for example pulling, pushing or twisting to charge a spring, may be difficult for a user to perform, particularly if the user is elderly or has dexterity problems.

However, two main user risks have been identified with such a device. Firstly, the user might press a trigger button several times or hold on to the trigger button for too long, causing multiple doses to be injected. Secondly, there would be a risk of the device being triggered accidentally.

In WO 02/47746 A1 a device for auto-injection of a dose of medicament is disclosed, comprising a housing arranged to contain a medicament container therein and comprising a contact part intended to be applied against an injection site, a needle cover surrounding a needle arranged to the medicament container and extending at least the length of the needle, spring means capable of, upon activation, pushing the needle past the end of the needle cover as well as operating said medicament container to supply the dose of medicament, first locking means capable of locking said spring means in a pressurised state, first activating means capable of, upon manual operation, releasing said spring means for injection, characterised by a second locking means capable of locking said first activating means and a second activating means, capable of releasing said second locking means when said contact part is exposed to pressure.

WO 2006/130098 A1 discloses a device for delivery of predetermined doses of liquid medicament. The device comprises a servo drive spring acting in the way of a clock spring for generating a torque. The torque is used for rotating a drum which advances a threaded plunger rod. The rotation of the drum may be blocked by a pin engaging with a slot when a dose of medicament has been delivered.

U.S. Pat. No. 6,972,007 B2 discloses a device for administering an injectable product in doses, the device comprising a dosing member connected to a locking means, which may be held in latching positions thus taking off a spring force onto a driven member which serves for advancing a piston and consequently for delivering a set dose of medicament. The locking means is held in the locking position by grooves engaging with corresponding protrusions.

WO 2006/045529 A1 discloses an injection device having a helical spring adapted to provide a force in the axial direction of the injection device for ejecting a dose of medicament. A rotary movement of a dose indicator barrel is caused by the force of the resilient member acting on a thread. The rotational movement may be manually blocked by appropriately switching a locking member between a locking state and an unlocking state.

WO 2007/063342 A1 discloses a pen-type injector for receiving a medication container. The injector comprises a housing and a torsion spring coupled to a drive member. A dose setting knob is coupled to the spring and rotatably coupled to a housing such that rotation of the knob in a first direction results in compression or twisting of the spring. A user actuable button is coupled to the housing for axial motion relative thereto, the button being coupled to the torsion spring to unwind or expand in discrete steps with each press of the button, which is achieved by engaging teeth of sprung legs of a clutch collet with a toothed rack.

SUMMARY

It is an object of the invention to provide a novel interlock mechanism for restricting a rotational movement of a rotatable component of a drug delivery device. Another object of the invention is to provide a novel drug delivery device. Yet another object of the inventtion is to provide a novel method for controlling the rotational movement of the rotatable component of the drug delivery device.

The object is achieved by an interlock means according to claim 1, by a drug delivery device according to claim 6 and a method according to claim 10.

Preferred embodiments of the invention are given in the dependent claims.

According to the invention an interlock mechanism for restricting a rotational movement of a rotatable component of a drug delivery device comprises:

a cam profile on the rotatable component, the cam profile with at least one catch and at least one cam;

a latch arm engageable with the catch for preventing rotation of the rotatable component;

a trigger arm engageable with a protrusion of the latch arm for pivoting the latch arm out of the catch by translative movement of the trigger arm thus allowing rotation of the rotatable component, the trigger arm pivotable by the cam during the subsequent rotation of the rotatable component for disengaging the trigger arm from the protrusion;

an interlocking means for catching and holding the trigger arm once the trigger arm has been translatively moved and pivoted;

reset means for releasing the trigger arm from the interlocking means.

For operating the interlock mechanism a method for controlling the rotational movement of the rotatable component of the drug delivery device is applied, the method comprising the steps of:

translatively moving the trigger arm engaged with the protrusion of the latch arm from an initial position for pivoting the latch arm out of one of at least one catches provided in the cam profile of the rotatable component thus allowing the rotatable component, biased by an energy source to rotate;

pivoting the trigger arm by one of at least one cams provided in the cam profile during the rotation of the rotatable component whereby the trigger arm is disengaged from the protrusion thus allowing the latch arm to re-engage with one of the catches to stop the rotational movement and whereby the interlock means catches and holds the trigger arm in its translatively moved and pivoted position until the interlock means is released by the reset means;

translatively moving the trigger arm back into the initial position once the interlock means is released thereby allowing it to pivot back and re-engage with the protrusion.

The interlock means according to the invention allows for restricting the rotational movement of the rotatable component until the latch arm re-engages with the catch. This happens after one full rotation when only one catch is provided in the cam profile or after a fraction of a full rotation when more than one catch is provided. Another rotation cannot be triggered unless the interlocking means releases the trigger arm. This can be performed by some kind of user action to ensure that the triggering is intentional. The interlock means may be applied for ensuring that only one dose of the drug is delivered at a time in a multi-dose drug delivery device with each full or partial rotation of the rotatable component. Thus a user is prevented from administering multiple doses, e.g. by pressing a trigger button more than once or by holding the trigger button pressed whilst a needle is inserted into his body. Before a second injection can be triggered the user must perform some action that preferably cannot take place without first removing the needle from the body. Therefore, it is highly unlikely that the user could accidentally reset the interlock mechanism whilst the needle is inserted into the body.

Similar interlock mechanisms may be designed for restricting translative movement of non-rotatable components.

The rotational movement may be transferred into a translative movement of a piston rod and a bung of a syringe by a screw thread on the piston rod, the translative movement of the bung resulting in delivery of a dose of the drug.

The rotational movement of the rotatable component may be caused manually. However it is preferred to bias the rotatable component by an energy source, such as a spring motor so it starts rotating as soon as the latch arm is disengaged from the catch. The spring motor may be in the shape of a coiled strip of spring steel stored on a first drum with one end of the spring steel connected to a second drum. The ends of the strip of spring steel may be held in slots provided in the first and second drum, respectively. The spring motor is charged by rotating the second drum. Thereby the flat spring is unwound from the first drum and wound back on itself in a figure-of-eight fashion to create a coil on the second drum. If the drums are released at this point the flat spring would tend to return to its original coiled state on the first drum and will thus cause both drums to rotate until the flat spring is completely transferred back onto the first drum.

The reset means for releasing the interlock means may be operated manually by operating a lever or the like. Preferably the reset means is automatically operated. For example the interlock means may be released when a safety cap is placed on the drug delivery device or when a needle of a syringe contained in the drug delivery device is changed, in particular when the interlock mechanism is used in multi-dose drug delivery devices for preventing it to deliver more than one dose at a time. The reset means may also be released when an injection site is contacted with the drug delivery device or the drug delivery device is pressed against the injection site, e.g. the user's skin.

In another embodiment the reset means may be operated when the safety cap is removed from the drug delivery device. This is particularly useful when the interlock mechanism is used for preventing accidental triggering of the drug delivery device, e.g. when carrying the device around in a bag.

When the interlocking mechanism is used in a one-shot drug delivery device the dose delivered during one rotation of the rotatable component may equal at least almost a total volume of the drug held in the syringe contained in the drug delivery device.

The drug delivery device may have a needle for delivering the drug through or into the skin. Alternatively the drug delivery device may be a jet injector with a jet nozzle for needle free injections. The drug delivery device may also be a dose inhaler device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The drug delivery device may be a fixed-dose delivery device where the device contains a number of fixed doses. It may also be a variable dose device.

BRIEF DESCRIPTION OF THE FIGURES

The present invention will become more fully understood from the detailed description given herein below and the accompanying drawings which are given by way of illustration only, and thus, are not limited of the present invention, and wherein:

FIG. 1A to 1F show a rotatable component of a drug delivery device with an interlock mechanism for controlling rotation of the rotatable component.

DETAILED DESCRIPTION

Figure 2:
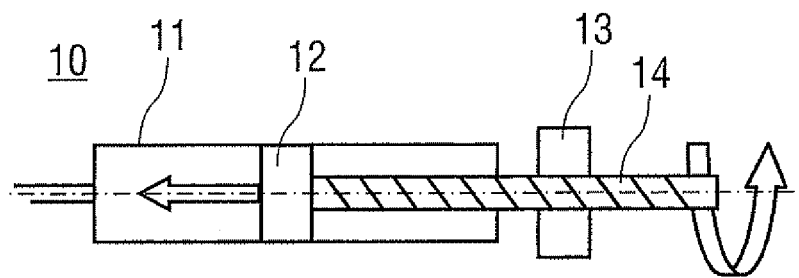
FIG. 2 is a schematic lateral view of a drug delivery device.

FIG. 1A shows a rotatable component 1 of a drug delivery device (not shown) with an interlock mechanism for controlling rotation R of the rotatable component 1. The embodiment shown is intended to be applied as a multiple-dose interlock mechanism that is suitable for a "screw" based autoinjector.

For the purposes of this description a "screw" based autoinjector mechanism is one where rotation of the rotatable component 1 about a longitudinal axis 2 (normal to the image plane of the figures) of the drug delivery device (autoinjector) causes a plunger/piston (not shown) to advance along a drug container body (syringe, not shown), forcing drug to be dispensed from the other end of the container (e.g. via a needle).

In this embodiment one dose of drug is delivered by one full rotation of the rotatable component 1.

The interlock mechanism comprises:

a cam profile on the rotatable component 1, the cam profile having a catch 3 and a cam 4;

a swivel mounted latch arm 5 engageable with the catch 3 for preventing rotation R of the rotatable component 1;

a swivel mounted and translatively moveable trigger arm 6 engageable with a protrusion 7 of the latch arm 5 for pivoting the latch arm 5 out of the catch 3 by translatively movement T of the trigger arm 6 thus allowing rotation R of the rotatable component 1, the trigger arm 6 pivotable by the cam 4 during the subsequent rotation R of the rotatable component 1 for disengaging the trigger arm 6 from the protrusion 7;

an interlocking means 8 for catching and holding the trigger arm 6 once the trigger arm 6 has been translatively moved and pivoted;

reset means (not shown) for releasing the trigger arm 6 from the interlocking means 8.

In FIG. 1A the interlock mechanism is in an initial state ready for triggering. The latch arm 5 is engaged with the catch 3 thus preventing rotation R of the rotatable component 1. The trigger arm 6 is in an initial position engaged with the protrusion 7 of the latch arm 5.

In FIG. 1B a trigger button 9 is pushed thereby translatively moving the trigger arm 6 out of its initial position. The trigger arm 6 engaged with the protrusion 7 of the latch arm 5 pivots the latch arm 5 out of the catch 3. The rotatable component 1, biased by an energy source such as a spring motor (not shown), now starts rotating as shown in FIG. 1C.

During the start of the rotation R of the rotatable component 1 the trigger arm 6 is pivoted by the cam 4. Thereby the trigger arm 6 is disengaged from the protrusion 7 thus allowing the latch arm to re-engage with the catch 3 after a full 360° rotation R. Also by pivoting the trigger arm 6 the interlock means 8, e.g. under tension of a spring catches and holds the trigger arm 6 in its translatively moved and pivoted position. The FIGS. 1C to 1E show the trigger arm 6 being held by the interlock means 8 in a kind of hook. Alternatively there could be a recess in the trigger arm 6 for engaging with the interlock means 8.

In FIG. 1D the 360° rotation R is almost complete. The trigger button 9 was released by the user and is returned to its initial position, e.g. by means of a spring. Pressing it again does not have an effect since the trigger arm 6 is decoupled from the trigger button 9.

In FIG. 1E the 360° rotation R is complete. The latch arm 5, e.g. biased by a spring is re-engaged with the catch 3 thus preventing further rotation. The trigger arm 6 is still held by the interlock means 8 so the rotatable component 1 cannot be triggered.

In FIG. 1F the interlock means 8 has been released by some kind of user action. The trigger arm 6, e.g. biased by a spring, is now free to return to its initial position and to re-engage with the protrusion 7 to allow another trigger cycle.

The interlock means 8 may be reset by means of a manual button. However, it is preferred that this could be accomplished "automatically" by the user upon replacing a device cap or changing a needle. For example, attaching the device cap might displace a rod that is connected directly to the interlock means 8.

The rotational movement R may be transferred into a translative movement of a piston rod and a bung of a syringe by a screw thread on the piston rod, the translative movement of the bung resulting in delivery of a dose of the drug.

The rotational movement R of the rotatable component 1 may be caused manually. However it is preferred to bias the rotatable component 1 by an energy source, such as a spring motor so it starts rotating as soon as the latch arm 5 is disengaged from the catch 3.

The reset means for releasing the interlock means may be operated manually by operating a lever or the like. Preferably the reset means is automatically operated. For example the interlock means may be released when a safety cap is placed on the drug delivery device or when a needle of a syringe contained in the drug delivery device is changed. The reset means may also be released when an injection site is contacted with the drug delivery device or the drug delivery device is pressed against the injection site, e.g. the user's skin.

In another embodiment the reset means may operated when the safety cap is removed from the drug delivery device.

When the interlocking mechanism is used in a one-shot drug delivery device the dose delivered during one rotation of the rotatable component may equal at least almost a total volume of the drug held in the syringe contained in the drug delivery device.

The drug delivery device may have a needle for delivering the drug through or into the skin. Alternatively the drug delivery device may be a jet injector with a jet nozzle for needle free injections. The drug delivery device may also be a dose inhaler device.

The drug delivery device may be a fixed-dose delivery device where the device contains a number of fixed doses. It may also be a variable dose device.

The embodiment shown is intended for preventing a user from accidentally triggering the drug delivery device more than once.

Alternatively the interlock mechanism could be applied for accidentally triggering the drug delivery device at all. This interlock mechanism could work by disengaging the trigger button 9 from the dispensing mechanism. This could be accomplished in a similar manner to the multiple-dose interlock mechanism by detecting the presence of the device cap. The same component that detects the device cap, and connects to the multiple-dose interlock reset, could also form a key link between the external trigger button 9 and the dispensing mechanism trigger. When the cap is present this link feature would be displaced out of the chain between external trigger button and internal mechanism trigger. When the cap is removed the link feature would move into position between the external trigger button and mechanism trigger such that movement of the trigger button is transferred via the link feature to the mechanism trigger.

An alternative embodiment for the accidental-dose interlock would be for the cap of the device to physically prevent the trigger button 9 from being pressed.

The cam profile of the rotatable component may have more than one catch 3 and more than one cam 4. In this case the rotation R stops the re-engaging latch arm 5 and catch 3 after a fraction of a 360° rotation.

FIG. 2 shows a drug delivery device 10, comprising a container 11 for a fluid drug and a bung 12 for dispensing the dose, further comprising a drive mechanism with a telescopic piston comprising a driver 13 and a plunger 14 telescoped one in the other and connected to each other by a screw thread. The driver 13 may be rotated by a motor mechanism (not shown) while the plunger 14 is prevented from rotating, for example by means of a slot or the geometry of its external form. Thus, when the driver 13 is rotated the plunger 14 and the bung 12 are advanced and hence a dose of drug is dispensed from the container 11. The bung 12 does not necessarily have to be directly connected to the plunger 14.

Figure 3A:
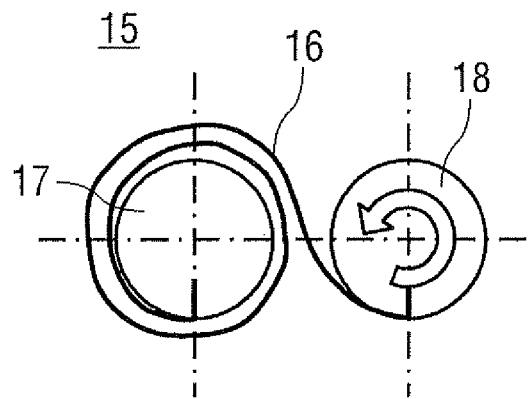
FIG. 3A, 3B show a schematic view of a motor mechanism for the drug delivery device.

FIG. 3A shows a schematic view of a motor mechanism 15 for the drug delivery device 10 in a relaxed state. The motor mechanism 15 contains a strip 16 of spring sheet metal, e.g. made of spring steel. Two drums are provided—a storage drum 17 and a torque drum 18. The coiled flat spring strip 16 is assembled over the storage drum 17 and one end of the flat spring strip 16 that is on the inside of the coil is connected to the storage drum 17, for example by passing the end of the strip 16 through a slot (not shown) in the storage drum 17. The torque drum 18 is assembled close to the storage drum 17 and the outside end of the flat spring strip 16 is connected to the torque drum 18, for example by passing the end of the strip 16 through a slot (not shown) in the torque drum 18.

Figure 3B:
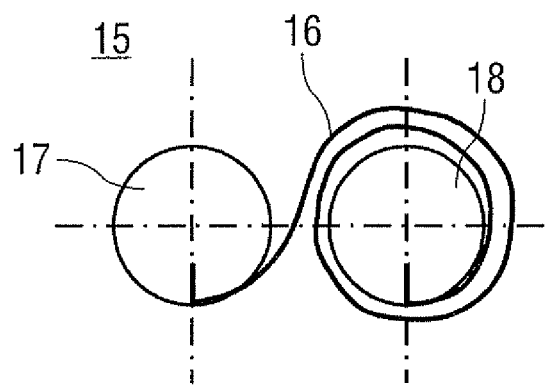

FIG. 3B shows the motor mechanism 15 in a charged state. The motor mechanism 15 is charged by rotating the torque drum 18. This may be done by manually rotating a spring reset dial. Typically in manufacture of a disposable drug delivery device 10 this would rather be done during production of the device in the factory with no manual dial in the device 1. The strip 16 is unwound from the storage drum 17 and wound back on itself in a figure-of-eight fashion to create a coil on the torque 18 drum. Thereby the strip 16 of spring sheet metal is bent the other way round than in the relaxed state thus arriving in the charged state with the strip 16 of spring sheet metal tending to re-coil onto the storage drum 17. If the drums 17, 18 are released at this point the strip 16 tends to return to its original relaxed state on the storage drum 17 and thus causes both drums 17, 18 to rotate until the strip 16 is completely transferred back onto the storage drum 17.

Figure 4:
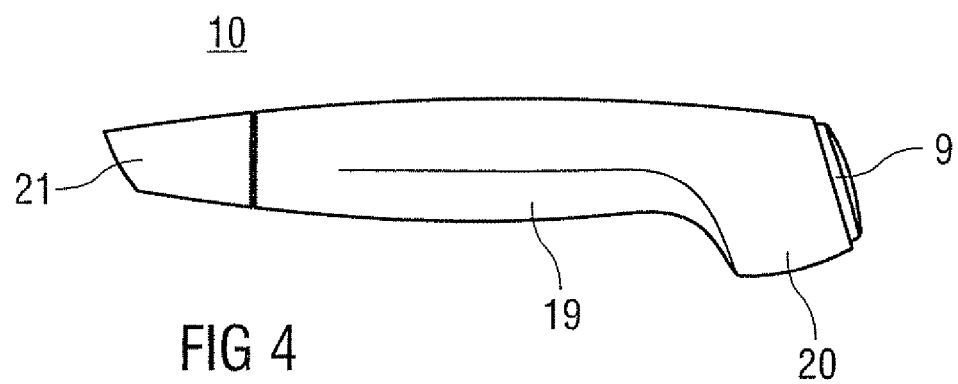
FIG. 4 shows a lateral view of the drug delivery device.

FIG. 4 shows a view of a possible embodiment of the drug delivery device 10, comprising a body 19 surrounding the components described in the FIGS. 1A to 3. At a back end of the body 19 a widened portion 20 is provided for housing the motor mechanism 15 with the two drums 17, 18 arranged side by side. The trigger button 9 is also arranged at the back end. At the opposite front end a device cap 21 is provided for securing the needle against accidentally being touched by the user.

The invention claimed is:

1. An interlock mechanism for restricting a rotational movement (R) of a rotatable component of a drug delivery device, the interlock mechanism comprising,
   a rotatable component having a cam profile, the cam profile comprising at least one catch and at least one cam;
   a latch arm having a protrusion configured to engage the catch, where the catch is configured to accept and hold the protrusion to prevent rotation (R) of the rotatable component;
   a pivotal trigger arm engageable with the protrusion of the latch arm for pivoting the latch arm out of the catch by translative movement (T) of the trigger arm thus allowing rotation (R) of the rotatable component, the trigger arm configured to engage the cam during rotation (R) causing the trigger arm to pivot and disengage from the protrusion;
   a resettable interlock configured to catch and hold the trigger arm once the trigger arm has been translatively moved and pivoted; and
   a reset configured to release the trigger arm from the interlock.

2. The interlock mechanism according to claim 1, characterized in that rotation (R) of the rotatable component causes delivery of a dose of the drug.

3. The interlock mechanism according to claim 1, characterized in that the rotatable component is biased by a spring motor.

4. The interlock mechanism according to claim 1, characterized in that the reset is operated manually or by placing a safety cap on the drug delivery device or by changing a needle of a syringe contained in the drug delivery device or by contacting an injection site with the drug delivery device.

5. The interlock mechanism according to claim 1, characterized in that the reset is operated by removing a safety cap from the drug delivery device.

6. A drug delivery device for administering a dose of a drug, the drug delivery device comprising a rotatable component causing delivery of the dose of drug when rotated, the drug delivery device further comprising an interlock mechanism according to claim 1 for restricting the rotation (R) of the rotatable component.

7. The drug delivery device according to claim 6, characterized in that multiple doses are administrable by a respective rotation (R) for each dose.

8. The drug delivery device according to claim 6, characterized in that the dose is equal to at least almost a total volume of the drug in a syringe contained in the drug delivery device.

9. The drug delivery device according to claim 6, characterized in that a needle or a jet nozzle is provided for delivering the drug.

10. A method for controlling a rotational movement (R) of a rotatable component of a drug delivery device by an interlock mechanism, the method comprising the steps of:
    translatively moving a trigger arm engaged with a protrusion of a latch arm from an initial position for pivoting the latch arm out of engagement and holding position by one of at least one catch provided in a cam profile of the rotatable component thus allowing the rotatable component, biased by an energy source, to rotate;
    pivoting the trigger arm by one of at least one cam provided in the cam profile during the rotation (R) of the rotatable component whereby the trigger arm is disengaged from the protrusion thus allowing the latch arm to re-engage with the at least one catch to stop the rotational movement (R) and whereby an interlock catches and holds the trigger arm in its translatively moved and pivoted position until the interlock is released by a reset;
    translatively moving the trigger arm back into the initial position once the interlock is released thereby allowing it to pivot back and re-engage with the protrusion.

11. The method according to claim 10, characterized in that the rotatable component is biased by a spring motor.

12. The method according to claim 10, characterized in that the reset is operated manually or by placing a safety cap on the drug delivery device or by changing a needle of a syringe contained in the drug delivery device or by contacting an injection site with the drug delivery device.

13. The method according to claim 10, characterized in that the reset is operated by removing a safety cap from the drug delivery device.

* * * * *